United States Patent
Woo et al.

(10) Patent No.: US 6,529,767 B1
(45) Date of Patent: Mar. 4, 2003

(54) METHOD AND APPARATUS FOR MEASURING SKIN MOISTURE BY USING NEAR INFRARED REFLECTANCE SPECTROSCOPY

(75) Inventors: Young Ah Woo, Seoul (KR); Hyo Jin Kim, Seoul (KR); Myung Yun Kim, Kwangyok-shi (KR)

(73) Assignee: Spectron Tech Co., Ltd., Seoul (KR)

( * ) Notice: Subject to any disclaimer, the term of this patent is extended or adjusted under 35 U.S.C. 154(b) by 0 days.

(21) Appl. No.: 09/675,122

(22) Filed: Sep. 28, 2000

(30) Foreign Application Priority Data

Sep. 1, 2000 (KR) ........................................ 2000-51489

(51) Int. Cl.[7] ............................................ A61B 6/00
(52) U.S. Cl. .................... 600/475; 600/477; 600/476; 600/473
(58) Field of Search .............................. 600/473, 475, 600/476, 477

(56) References Cited

U.S. PATENT DOCUMENTS 5,701,902 A * 12/1997 Vari et al. .................... 600/473
5,818,048 A * 10/1998 Sodickson et al. .......... 250/343
6,246,894 B1 * 6/2001 Steuer et al. ................ 600/322

OTHER PUBLICATIONS

Yamamura, Tatsuo, "Measuring methods of skin surface water content.", *Fragrance Journal*, 1993, pp. 35–42, vol. 10 (Japan).

Beebe, Kenneth R., et al., "An Introduction to Multivariate Calibration and Analysis", *Analytical Chemistry*, Sep. 1, 1987, 9 pp., vol. 59, No. 17.

Martin, Kathleen A., "Direct Measurement of Moisture in Skin by NIR Spectroscopy", Journal of the Society of Cosmetic Chemists, Sep./Oct. 1993, pp. 249–261, vol. 44.

Martin, Kathleen, "In Vivo Moisturization of Water In Skin by Near–Infrared Reflectance", *Applied Spectroscopy*, 1998, pp. 1001–1007, vol. 52, No. 7, Society for Applied Spectroscopy.

* cited by examiner

Primary Examiner—Marvin M. Lateef
Assistant Examiner—Runa Shah Qaderi
(74) Attorney, Agent, or Firm—Webb Ziesenheim Logsdon Orkin & Hanson, P.C.

(57) ABSTRACT

A set of reference moisture value of the plurality of sample skin is measured with conventional skin moisture measuring device. Then a set of standard calibration equation is provided from calculating a set of measured reflectance spectra of calibration and the set of reference moisture value by using the multivariate regression, and it is stored at a memory. The next steps are to measure skin moisture of test skin with reference to the set of standard calibration equation stored at the memory. By radiating near infrared on the test skin and sensing a set of reflectance spectra with the portable skin moisture measuring apparatus by using near infrared reflectance spectroscopy system, the skin moisture is measured at a repeatable and stable way, regardless of the variation of temperature or humidity of the external circumstance.

9 Claims, 6 Drawing Sheets

| PRETREATMENT | FACTOR | SEC | SEP |
|---|---|---|---|
| NO PRETREATMENT | 7 | 5.18 | 5.86 |
| FIRST ORDER DERIVATIVE | 6 | 4.77 | 5.59 |
| SECOND ORDER DERIVATIVE | 6 | 4.60 | 6.06 |

METHOD AND APPARATUS FOR MEASURING SKIN MOISTURE BY USING NEAR INFRARED REFLECTANCE SPECTROSCOPY

BACKGROUND OF THE INVENTION

1. Field of the Invention

This invention generally relates to a method and apparatus for measuring skin moisture by using near infrared reflectance spectroscopy, and more particularly relates to measuring skin moisture without destroying the test object, and producing a portable skin moisture measuring apparatus.

2. Background of the Invention

The skin is a structure consisting of both epidermis and dermis combination. The softness and pliability are the main characteristic factors of skin surface protecting the body and securing the motion of the body. Such characteristic factors are dependent on the amount of moisture contained in the stratum corneum layer, which is the outermost layer of the skin, and controlled by the barrier function and moisture maintaining function of the skin layer.

The stratum corneum is about 20 micron thick, and composed of partially dehydrated cells in a liquid matrix. Between the cells are lipid mixture called stratum corneum intercellular lipid, which composes the barrier of the skin. The lipid mixture is composed of cell amide, cholesterol, free fatty acid, and cholesterol sulfate, secreted from intercellular lamella granular when epidermis cells are transferred from granular layers to stratum corneum, and formed between the stratum corneums.

If normal stratum corneum is not properly developed due to environmental changes and diseases, the barrier function and moisture maintaining function of the skin is lowered. In such situation, the face of the skin becomes easily dried, roughed and cleaved if the moisture of stratum corneum is not sufficiently maintained. Therefore, it is very important to maintain the amount of moisture in the stratum corneum of the skin properly.

However, in modern life, it is difficult to maintain healthy skin due to various pollution and rapid environmental changes. For the above reasons, most people are using a skin moisture lotion in their daily life. In order to maintain healthier skin, it is essential to measure the density of skin moisture and check skin conditions periodically. Although such works can be done by cosmeticians or dermatologist, skin moisture measuring devices are rarely used. Conventional skin moisture measuring devices are utilized at laboratories for research purpose only, because price of those devices are too expensive, and the devices are easily influenced by temperature and humidity changes, which requires to be kept at a constant temperature and humidity conditions.

The infrared spectroscopy and high frequency impedance method are widely used for conventional skin moisture measuring apparatus and method. The infrared spectroscopy is a direct moisture measuring method at certain wavelength range. As the measuring device utilizing the method is not only very expensive because it uses Fourier Transform infrared spectroscopy device using the total reflection absorption method, but also difficult to operate, it is rarely used for commercial purpose devices.

Therefore, devices utilizing the high frequency impedance method have been widely used so far. The devices are utilizing the fact that when a large amount of electrolytes, such as salts and amino acid, are contained in the stratum corneum layer, the electrolytes make the surface of the skin electrically conductive. Therefore, if the alternating current having a constant frequency is applied, electric conductance that is the reciprocal of the resistance that consists of impedance is measured, and the skin moisture is calculated from the electric conductivity that has dependency on the skin moisture.

However, because the conventional skin moisture measuring method using the high frequency impedance method is easily affected by environmental conditions, such as temperature or humidity changes, it does not provide the correct skin moisture value if external environmental conditions change. Moreover, the above method is influenced by the amount of electrolyte that the test skin contains, which is another problem of the skin moisture measuring method using the high frequency impedance method.

Moreover, the size of the conventional skin moisture measuring devices is too big and spacey, and it is too heavy to carry.

SUMMARY OF THE INVENTION

The present invention is to provide the method and apparatus for measuring skin moisture by using near infrared reflectance spectroscopy that is improved with respect to the conventional methods and apparatuses.

An object of the present invention is to provide small sized portable skin measuring devices using near infrared reflectance spectroscopy, which is not influenced by environmental conditions such as temperature and humidity changes.

Another object of the present invention is to provide a skin-measuring device that is fast and convenient to use.

These objects may be accomplished with the method and apparatus using Near Infrared Reflectance Spectroscopy (NIRS).

One aspect of the present invention is to provide the method for measuring skin moisture using near infrared reflectance spectroscopy.

A set of reference moisture values of a plurality of sample skin is measured with conventional skin moisture measuring device.

And then providing a set of standard calibration equation of the plurality of sample skin is processed as follows: radiating near infrared on the plurality of sample skin, sensing a set of near infrared reflectance spectra reflecting from the plurality of sample skin, dividing the set of reflectance spectra into a calibration set and a validation set by using random selection, analyzing with multivariate regression the calibration set and the set of reference moisture value to produce a set of standard calibration equation of the plurality of sample skin, and then evaluating and correcting the set of standard calibration equations by using the validation set. Thereafter, the set of standard calibration equations is stored at a memory.

Next step is the process of measuring skin moisture by using near infrared reflectance spectroscopy with reference to the set of standard calibration equation stored at the memory. The process includes radiating near infrared on a test skin, sensing a near infrared reflectance spectrum reflecting from the test skin, and then introducing the near infrared reflectance spectrum from the test skin into the set of standard calibration equations stored at the memory to calculate the skin moisture of the test skin.

Another aspect of the present invention is an apparatus to measure skin moisture using near infrared reflectance spectroscopy comprising the means of storing a set of standard skin moisture calibration equation of the plurality of sample skin, radiating near infrared on a test skin, sensing a near infrared reflectance spectrum reflecting from the test skin, predicting the skin moisture of the test skin from the near infrared reflectance spectrum reflecting from the test skin and the set of standard calibration equation stored at the memory.

DETAILED DESCRIPTION OF THE INVENTION

Figure 1:
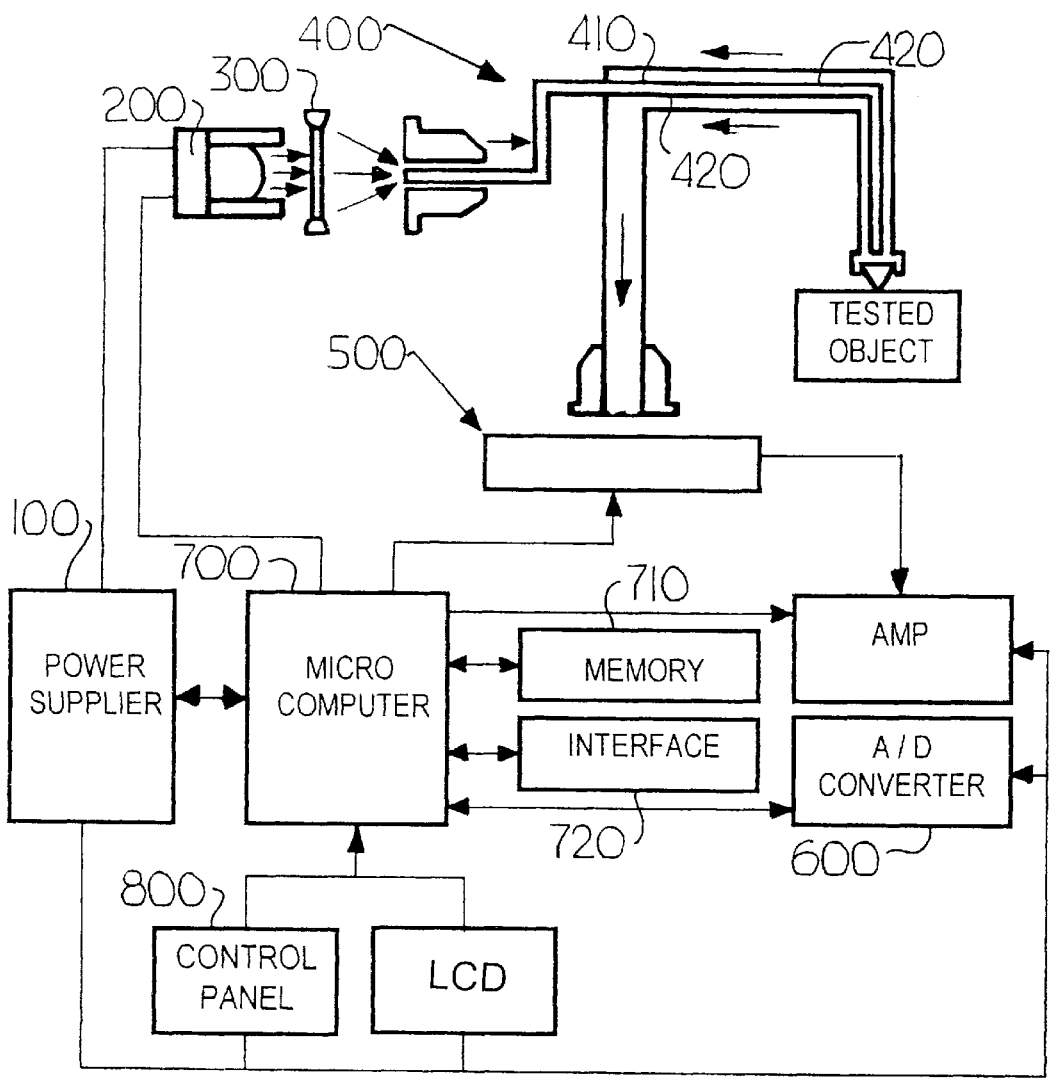
FIG. 1 is a block diagram generally representing the configuration of the portable skin moisture measuring apparatus of the present invention, which is using near infrared reflectance spectroscopy.
Figure 2:
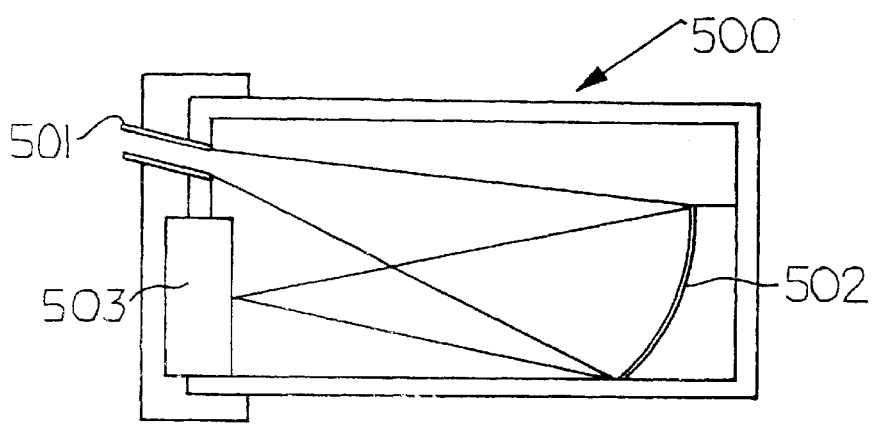
FIG. 2 is a block diagram generally representing the configuration of the chip-type spectrometer of the near infrared reflectance spectroscopy.

Referring now to FIG. 1 and FIG. 2, there is illustrated an apparatus for measuring skin moisture by using near infrared reflectance spectroscopy according to the present invention. FIG. 1 is a block diagram of a portable skin moisture measuring apparatus using near infrared reflectance spectroscopy, and FIG. 2 is a block diagram of a chip type spectrometer applying to a portable skin moisture measuring apparatus.

Referring to FIG. 1, the apparatus of the present invention includes power supplier 100, tungsten halogen lamp 200, optical filter 300, optical cable 400, chip type spectrometer 500, amplifier, A/D converter 600, microcomputer 700, control panel 800 and LCD panel.

The power supplier 100 includes batteries (not depicted) to provide 612 voltage to each element of the apparatus according to the control signal inputted.

The tungsten halogen lamp 200 is designed to generate near infrared of which wavelength ranges from 500 nanometers to 2000 nanometers upon receiving a control signal from the microcomputer and power from the power supplier 100.

The optical filter 300 is placed along the optical route of the tungsten halogen lamp 200 to focus the near infrared waves generated from the tungsten halogen lamp 200.

The optical cable 400 is formed to radiate near infrared on the test skin and to transmit the near infrared reflectance spectra to the spectrometer 500. The internal cable 410 of the optical cable 400 transmits near infrared radiated through the optical filter 300 to the test skin, and the external cable 420 transmits near infrared reflected from the skin to the spectrometer 500.

Referring to FIG. 2, the chip type spectrometer 500 is a reflectance light sensor. The spectrometer 500 includes a light incidence slot 501 through which the reflectance light is entered, a self-focusing grating 502 formed at a corresponding location to the light incidence slot 501 to divide and reflect the near infrared reflectance spectra radiated through the light incidence slot 501, and a photo diode array detector 503 formed at a corresponding location to the self-focusing grating 502 to sense the near infrared reflectance spectra of which wavelength ranges from 1100 to 1750 nanometer reflected from the self-focusing grating 502 at 10 nanometers interval along the photo diode array, and transform the sensed near infrared reflectance spectra into electric signal.

The amplifier is connected to the output of the photo diode array detector 503 of the spectrometer 500 to amplify the electric signal outputted from the spectrometer 500 to a voltage level higher than predetermined voltage according to the inputted control signal from the microcomputer 700.

The A/D converter 600 is formed to convert analog signal outputted from the amplifier to digital signal according to the control signal from the microcomputer 700.

The microcomputer 700 controls every function of the apparatus of the present invention. It is designed to control the tungsten halogen lamp 200 and chip type spectrometer 500 to generate near infrared when a measurer operates the function keys at the control panel 800 to measure skin moisture. Moreover, the microcomputer 700 applies digital signal, which is outputted from the photo diode array detector 503 of the spectrometer 500 through the amplifier and the AID converter 600, to the standard calibration equation stored at the memory 710 to calculate the skin moisture of the test skin, and displays the calculated skin moisture to the user. It is preferable to further comprise an interface 720 to transmit and receive data to and from the external devices.

Memory 710 is a Read Only Memory (RAM) where both the data for operating the system and the standard skin moisture calibration equation are stored.

The control panel 800 is composed of a plurality of digit keys, menu keys, and function keys to produce control signal, when user manipulates each key.

The LCD panel displays skin moisture and state of the system, reflecting the control signal.

Referring now to the FIG. 3 to FIG. 9, the method for measuring skin moisture by using near infrared reflectance spectroscopy of the present invention is illustrated.

Prior to explaining the function of the present invention, the near infrared reflectance spectroscopy will be introduced briefly. The near infrared reflectance spectroscopy is a nondestructive test in which pretreatment is rarely required. The NIR spectroscopy is using the absorption energy and combination bands of infrared absorption of vibration energy of —CH, —NH, or —OH bands.

Though the near infrared was discovered by William Herschel in 1800, research was not progressed due to big noise and weak signal properties. Instruments designed especially for operation in the near infrared have been commercially available since early 1960 as a result of the pioneering work of K. Norris applying a multivariate analysis to the complicated near infrared spectrum to analyze the chemical solid object of agricultural products, and their area of application has since been broadened to not only foods, textile, petroleum chemicals and polymer, but also to the medical industry. The near infrared reflectance spectroscopy minimizes the pretreatment to the test object and enables a fast analysis. Moreover, it has merits in that it is a nondestructive analysis measuring plural elements simultaneously and repeatedly on a real time basis.

As described in the above, the standard calibration equation of skin moisture measured from the plurality of sample skin is stored at the memory 710. A more detailed description on the process of providing the standard calibration equation of skin moisture and storing the equation data at the memory is illustrated referring to FIG. 3 or FIG. 9.

Figure 3:
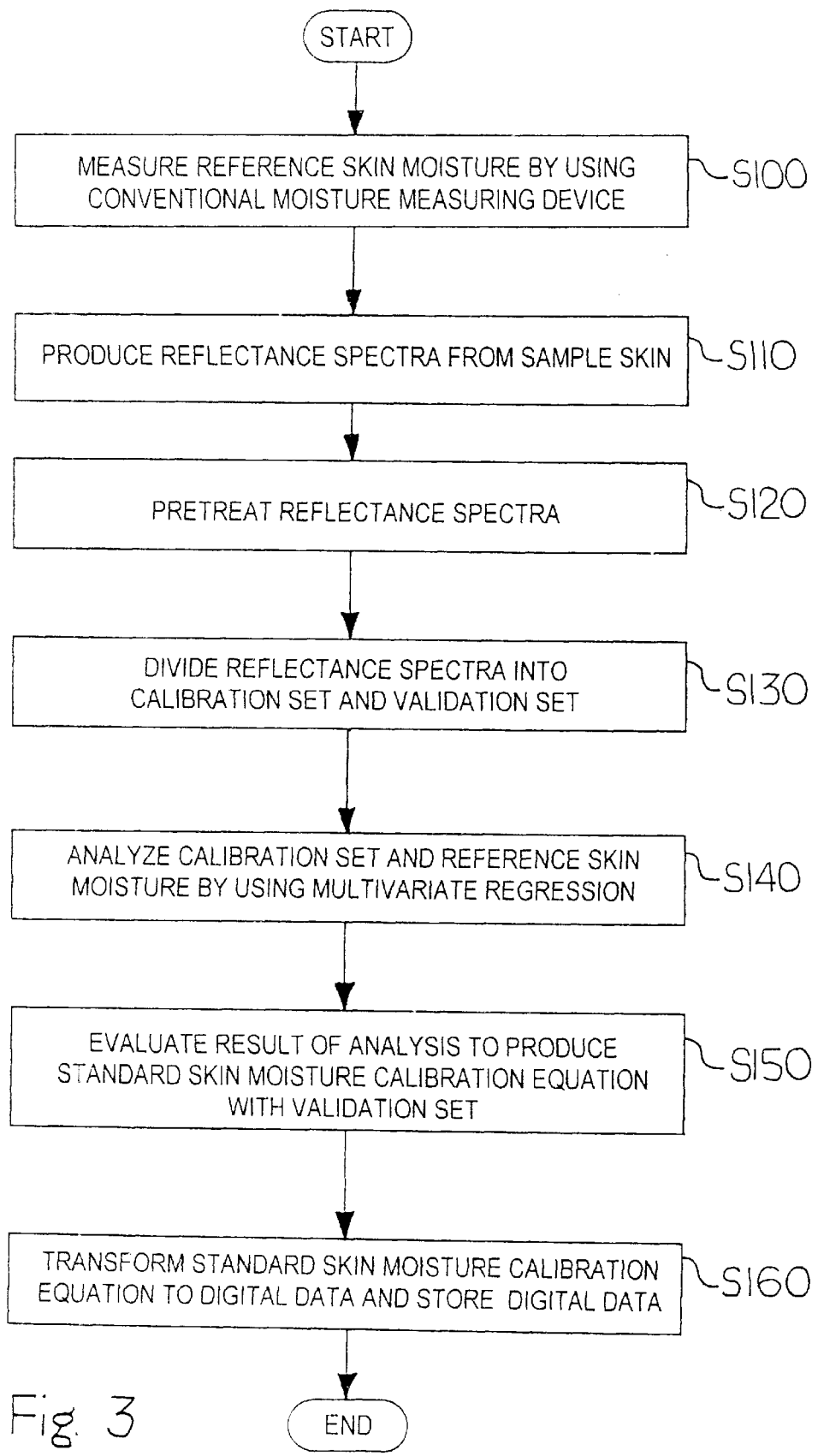
FIG. 3 is a flowchart representing the process how to store a set of standard calibration equation at the memory of a portable skin moisture measuring apparatus, according to the present invention.
Figure 4:
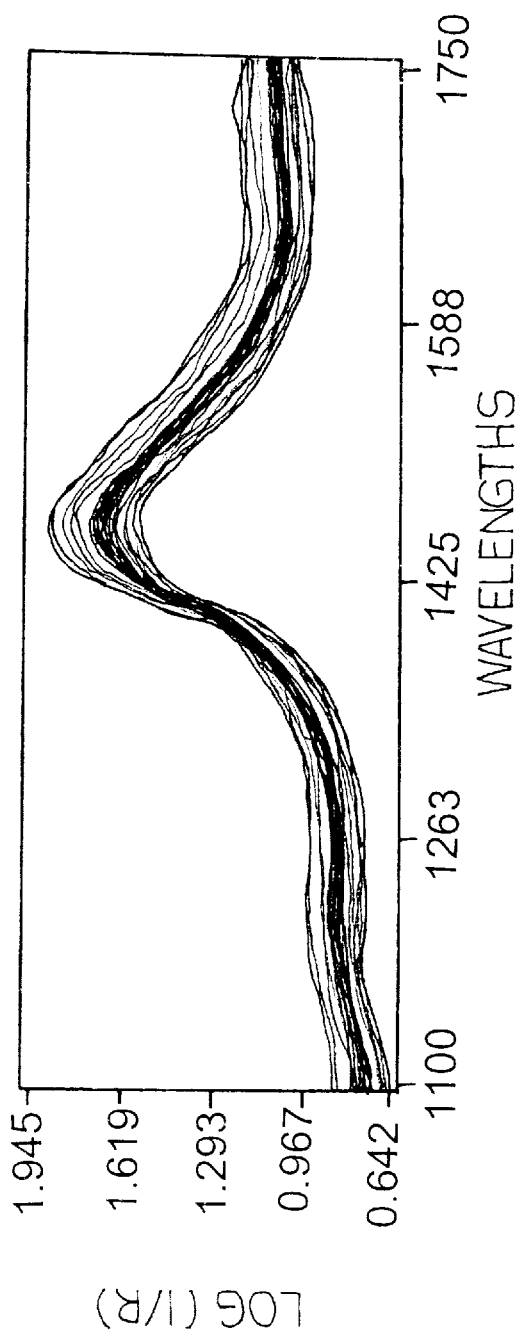
FIG. 4 depicts a set of near infrared reflectance spectra reflecting from the plurality of a sample skin.
Figure 5:
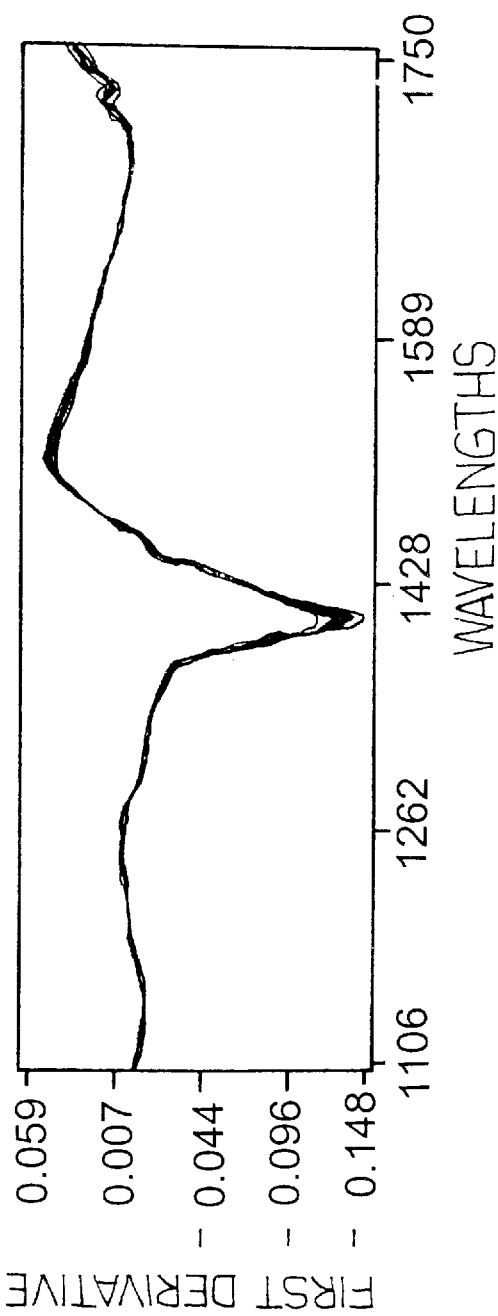
FIG. 5 depicts a set of the first derivative spectra of the FIG. 4 spectra.
Figure 6:
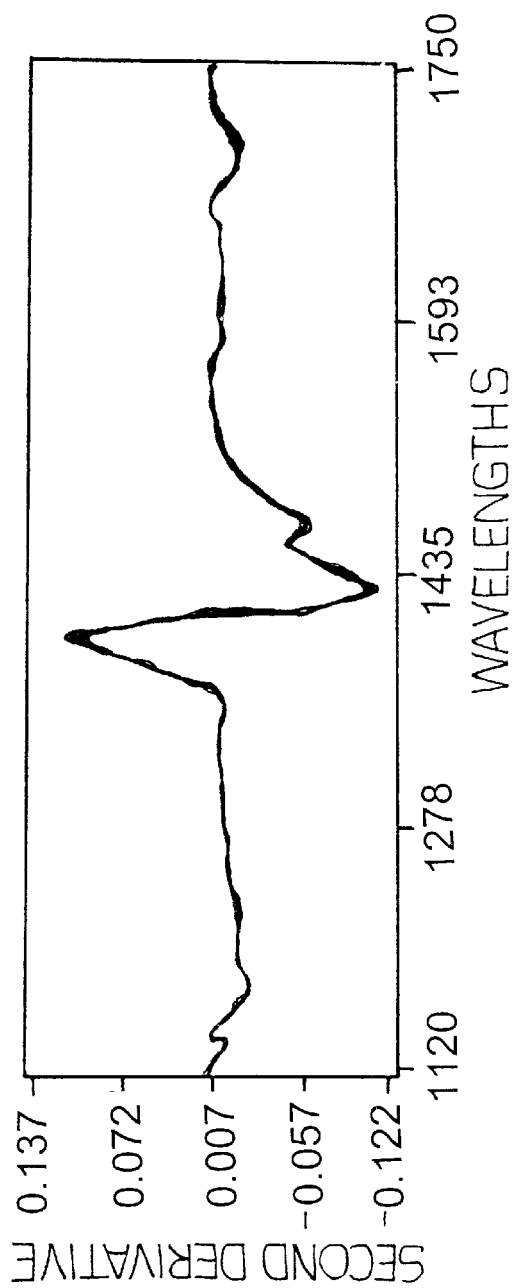
FIG. 6 depicts a set of the second derivative spectra of the FIG. 4 spectra.
Figure 7:
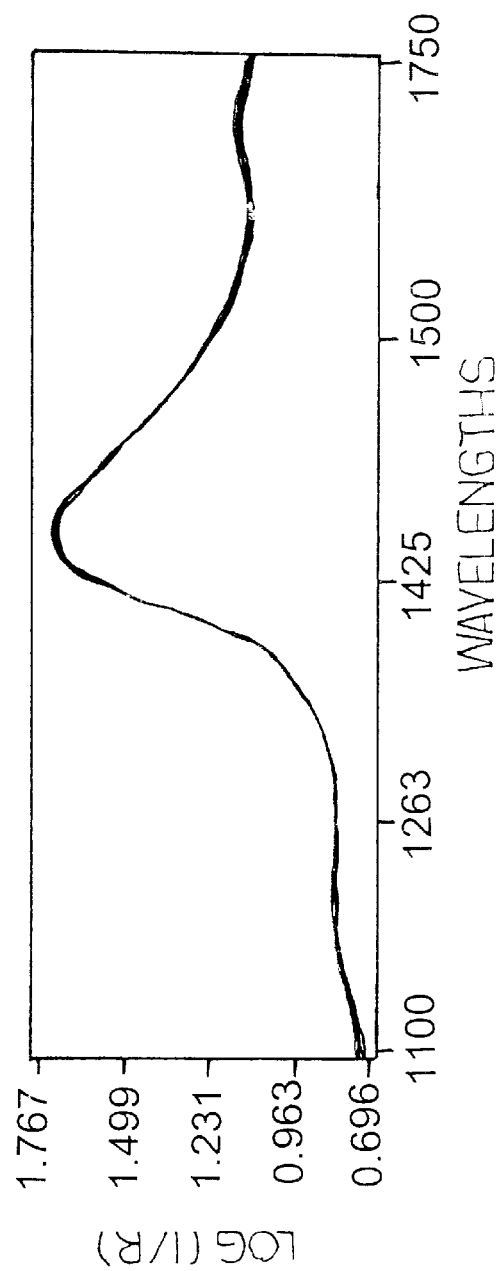
FIG. 7 depicts a set of multiplicative scatter corrected spectra of the FIG. 4 spectra.
Figures 8, 9:
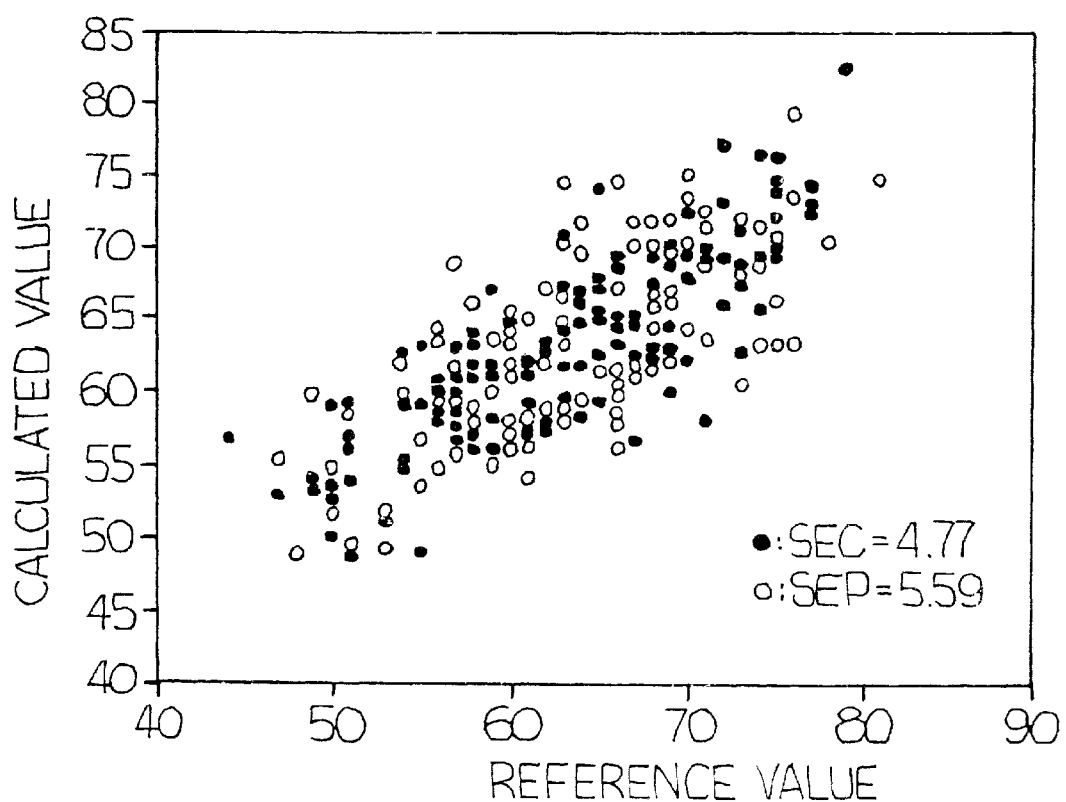
FIG. 8 is a table showing the result of calculating the spectra of FIGS. 4, 5, and 6 with PLSR.
FIG. 9 depicts a scatter plot showing correlation between NIR calculated moisture value and reference moisture value.

FIG. 3 is a flowchart on the process of how to store a set of standard calibration equation at the memory of a portable skin moisture measuring apparatus, according to the present invention. FIG. 4 is a set of near infrared reflectance spectra reflecting from the plurality of sample skin. FIG. 5 is a set of first derivative spectra of the FIG. 4 spectra. FIG. 6 is a set of second derivative spectra of the FIG. 4 spectra. FIG. 7 is a set of multiplicative scatter corrected spectra of the FIG. 4 spectra. FIG. 8 is a table of the result of calculating the spectra of FIGS. 4, 5, and 6 with partial least squares regression (PLSR). FIG. 9 is a scatter plot showing correlation between NIR calculated moisture value and reference moisture value.

A preferred embodiment of the present invention is described by referring to FIG. 3. In the embodiment, the number of test people is 15, and 16 samples are taken from sample skin of each test person, particularly from the inside skin of the arm, by using Corneometer CM 825, which is a conventional moisture measuring device using electric conductivity, and produces a total of 240 reference moisture values of the plurality of sample skin (S100).

The near infrared is radiated to the 16 skin locations of each of the 15 test people by using near infrared reflectance spectroscopy to produce 240 near infrared reflectance spectra reflecting from the sample skin (S110), wherein the skin locations and the test people are the same as those measured by Corneometer CM 825 described above. FIG. 4 depicts a set of near infrared reflectance spectra reflecting from the plurality of sample skin. FIG. 4 shows a huge band between 1400 to 1500 nanometers, due to the first O-H overturn band of water.

As scattering effects of the reflectance spectra are different from each other depending on location of the skin measured and test people, the reflectance spectra may be pretreated to reduce the effect (S120).

At an embodiment of the present invention, the sensed set of near infrared reflectance spectra reflecting from the plurality of sample skin may be pretreated by performing either first derivatives or second derivatives. The sensed set of near infrared reflectance spectra are the first derivative or second derivative, and the set of spectra derivative are shown at FIG. 5 or FIG. 6. Wherein, the segment and smooth of the first derivative may be 4 unit and 4 respectively, and segment and smooth of the second derivative may be 8 unit and 6 respectively.

In another embodiment of the present invention, the sensed set of near infrared reflectance spectra reflecting from the plurality of sample skin may be pretreated by performing a multiplicative scatter correction. The sensed set of near infrared reflectance spectra, which is multiplicative scatter corrected is shown at FIG. 7.

According to the multiplicative scatter correction, the correlation between each sensed reflectance spectra and average spectrum of near infrared reflecting from the plurality of sample skin is represented as Linear Regression Equation, from which segment a and gradient b are produced, then the sensed spectra are compensated by the segment a and gradient b as following equations.

$$x_k = a + b\bar{x}_k + e_k$$

$$x_{k,corrected} = (x_k - a)/b$$

Wherein, $x_k$ is spectrum data at wavelength k, and $\bar{x}_k$ is average spectrum of the sample set.

At another embodiment of the present invention, the sensed set of near infrared reflectance spectra reflecting from plurality of sample skin may be pretreated by multiplicative scatter correction and pretreated continuously by either first derivatives or second derivatives. The order of the pretreatment can be changed.

The next step is dividing the set of reflectance spectra into calibration set and validation set by using random selection, where each divided set has 120 spectra. For the embodiment that the set of reflectance spectra are pretreated, the pretreated set of reflectance spectra is divided into calibration set and validation set (S130).

The calibration set is used for producing a calibration equation, and the validation set is used for evaluating the calibration equation.

As shown in step 140 of FIG. 3, the calibration set of reflectance spectra and the set of reference moisture value which was provided from the step 100 are analyzed by performing partial least squares regression (PLSR) which is one of the multivariate regressions so as to produce standard skin moisture calibration equation.

In the above embodiment, after the sensed set of near infrared reflection spectra is pretreated, the pretreated set is divided into calibration and validation sets, then the pretreated calibration set and reference moisture value set are analyzed by multivariate regression to produce the standard skin moisture calibration equation. In another embodiment of the present invention, the pretreatment process may be done after the set of the near infrared reflection spectrum is divided into calibration set and validation set.

The set of standard skin moisture calibration equation, which is produced by using the multivariate regression, is evaluated by using the validation set divided at the step 130. The result of the evaluation is shown at the FIG. 8.

FIG. 8 shows factors, Standard Error of Calibration (SEC), and Standard Error of Predictions (SEP) for three conditions depending on the pretreatment. The near infrared within the range of 1150 to 1650 nanometers wavelength is radiated to produce a set of reflectance spectra from the plurality of sample skin, then the set of reflectance spectra is calculated by using PLSR, the result of which is shown at the second row of the table of FIG. 8. As described above, the set of reflectance spectra from the plurality of the sample skin may be pretreated before calculation by using PLSR, the third row of the table shows the result of calculating the set of first derivative reflectance spectra by using PLSR, and the fourth row of the table shows the result of calculating the set of second derivative reflectance spectra using PLSR.

The factor shown at the table explains a variation of the spectra. The first factor explains more than 90% of the total variation of the spectra. And the second factor, which is orthogonal to the first factor, explains the rest of the variation not explained by the first factor. And, consecutively, remaining factors explain the remaining variation not explained by the preceding factors. Substantially, the factors representing significant information, not signal noise, are selected for the calibration equation.

SEC means a standard error value calculated from the calibration set to evaluate the correct standard calibration when providing a standard calibration equation. SEP means a standard error value calculated from the validation set to evaluate whether the provided calibration equation is correct. Therefore, the smaller the difference between the reference skin moisture value measured by conventional skin moisture measuring device and the skin moisture value calculated by using the NIR spectroscopy, which is represented by SEC and SEP, the provided calibration equation becomes more correct.

According to the FIG. 8, the first derivative set of reflectance spectra calculated by using PLSR has the least error, which is represented by either SEC or SEP. Here, the SEC is 4.77 and the SEP is 5.59. FIG. 9 shows a scatter plot showing correlation between NIR calculated moisture value and reference moisture value. The NIR calculated moisture value means the predicted value by using the method of present invention, and the reference moisture value means the measured value by using the conventional moisture-measuring device, the latter value was acquired at step 100. As the magnitude of the predicted value and the measured value are more similar each other, the predicted value is considered to be more accurate.

The calculated standard skin moisture calibration equation is transformed to digital standard skin moisture calibration data, and the digital standard skin moisture calibration data is then stored at the memory (710), as shown at the step 160.

Figure 10:
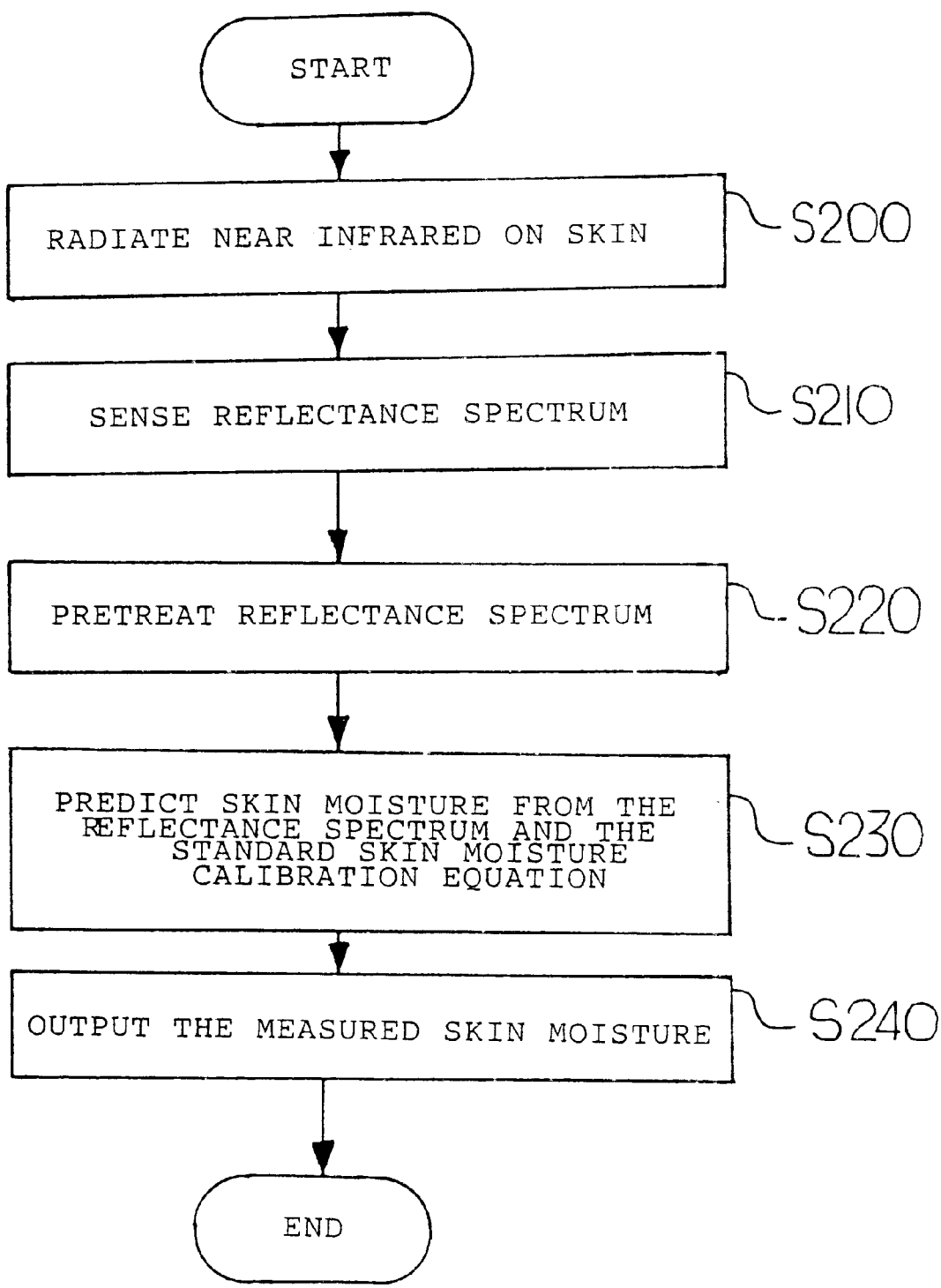
FIG. 10 is a flowchart to measure skin moisture using portable near infrared reflectance spectroscopy.

FIG. 10 is the flowchart illustrating process of measuring skin moisture by using near infrared reflectance spectroscopy of the present invention.

For measuring skin moisture of the test people, one end of the optical cable 400 is fixed on the optical filter 300, and other end of the optical cable 400 is fixed on the face or skin of the test people, and then, the control panel 800 is switched ON.

The near infrared generated from the tungsten halogen lamp 200 is focused by optical filter 300, then radiated to the skin of the test people through the optical cable 400 (S200).

When the power is switched on, the microcomputer 700 produces a control signal to operate the photo diode array detector 503 of the spectrometer 500.

The near infrared generated from the tungsten halogen lamp 200 and radiated to the skin of the test people is reflected from the skin to generate reflectance spectrum, then the reflectance spectrum is radiated to the chip type spectrometer 500, and the chip type spectrometer 500 senses the reflectance spectrum at 10 nanometers interval along the photo diode array, then generates an electric signal depending on the amount of the reflectance spectrum, and finally outputted to the amplifier (S210).

The amplifier amplifies the inputted electric signal to the predetermined magnitude, and then the amplified signal is inputted to the A/D converter 600, which converts the analog signal outputted from the amplifier into digital signal according to the control signal from the microcomputer 700, and then outputs the converted digital signal to the microcomputer 700. The converted signal is introduced to the standard calibration data stored at the memory 710, and then the skin moisture is calculated from the standard calibration data. (S230).

In an embodiment of the present invention, the reflectance spectrum may be pretreated before being introduced to the standard calibration data. However, in another embodiment of the present invention, where no pretreatment was performed at the digital standard skin moisture calibration data producing process, no pretreatment is performed at the skin moisture measuring process.

The pretreatment performed at the pretreatment step (S220) should be the same as the pretreatment performed for producing the standard calibration data stored at the memory 710, as shown at the step 120. Therefore, in an embodiment of the present invention where pretreatment was performed when the standard calibration data was produced, the pretreatment step (S220) should be performed. As illustrated at the digital standard skin moisture calibration data producing process, the pretreatment includes either pre-determined order of derivative or multiplicative scatter correction, or both. Whereas, in another embodiment of the present invention where no pretreatment was performed when the standard calibration data was produced, the pretreatment step (S220) is not performed at the skin moisture measuring process.

The measured skin moisture is displayed on an LCD panel. And in another embodiment of present invention, the measured skin moisture is printed out by a printing device. The microcomputer 700 is connected to the LCD panel or the printing device through the interface part 720. A type of skin, such as VERY DRY, DRY, or SUFFICIENT may be displayed on the LCD panel, the type is determined depending on the density of skin moisture.

As described above, the present invention provides skin moisture measuring method and apparatus which is repetitive and stable against the variation of temperature or humidity. Moreover, the measuring apparatus provided by the present invention can be small enough to be conveniently carried. Therefore, it enables skin moisture to be measured at any time and at any place.

Obviously, the numerous modifications and variations of the present invention are possible in light of the above teachings. It is therefore to be understood that within the scope of the attached claims, the invention may be practiced otherwise than as specifically described herein.

What is claimed is:

1. A method for measuring skin moisture of test skin, comprising the steps of:

measuring a set of reference skin moisture values on a plurality of sample skins by using a conventional skin moisture measuring device;

radiating near infrared light having a continuous wavelength ranging from 1100 nm to 1750 nm on the plurality of sample skins;

detecting a set of near infrared reflectance spectra reflecting from the plurality of sample skins;

dividing the set of near infrared reflectance spectra into a calibration set and a validation set by random selection;

analyzing, with multivariate regression, the calibration set and the set of reference moisture value to produce a set of standard calibration equation data of the plurality of sample skins;

correcting the set of standard calibration equation data using the validation set;

storing the set of corrected standard calibration equation data at a memory;

radiating near infrared light having a continuous wavelength ranging from 1100 nm to 1750 nm on the test skin;

detecting a near infrared reflectance spectrum reflecting from the test skin at a predetermined wavelength interval; and predicting the skin moisture of the test skin from the detected near infrared reflectance spectra from the test skin by using the stored standard calibration equation data.

2. A method as claimed in claim 1, further comprising the step of:

pre-treating the near infrared reflectance spectra reflecting from either the plurality of sample skins and the test skin with either pre-determined order of derivative or multiplicative scatter correction, or both.

3. A method as claimed in claim 2, wherein the pre-determined order of derivative is performing either first derivative or second derivative.

4. A method as claimed in claim 3, wherein the segment and smooth of the first derivative are 4 unit and 4 respectively, and segment and smooth of the second derivative are 8 unit and 6 respectively.

5. A method as claimed in claim 2, further comprising the step of displaying the skin moisture of the test skin.

6. A method as claimed in claim 2, further comprising the step of printing the skin moisture of the test skin.

7. A method as claimed in claim 1, further comprising the step of:

displaying the skin moisture of the test skin with a display screen.

8. A method as claimed in claim 1, further comprising the step of:

printing the calculated skin moisture of the test skin.

9. A method as claimed in claim 1, wherein the multivariate regression is performed with Partial Least Squares Regression.

* * * * *

UNITED STATES PATENT AND TRADEMARK OFFICE
CERTIFICATE OF CORRECTION

PATENT NO.    : 6,529,767 B1
DATED         : March 4, 2003
INVENTOR(S)   : Woo et al.

It is certified that error appears in the above-identified patent and that said Letters Patent is hereby corrected as shown below:

Column 4,
Line 37, "AID converter" should read -- A/D converter --.

Column 7,
Line 58, "AID converter" should read -- A/D converter --.

Signed and Sealed this

Eighth Day of July, 2003

JAMES E. ROGAN
*Director of the United States Patent and Trademark Office*